United States Patent [19]

Jaeggi

[11] Patent Number: 5,457,094

[45] Date of Patent: Oct. 10, 1995

[54] HETEROCYCLIC AMIDINES USEFUL FOR TREATING DISEASES ASSOCIATED WITH CALCIUM METABOLISM

[75] Inventor: Knut A. Jaeggi, Basle, Switzerland

[73] Assignee: Ciba-Geigy Corporation, Ardsley, N.Y.

[21] Appl. No.: 384,882

[22] Filed: Feb. 7, 1995

Related U.S. Application Data

[62] Division of Ser. No. 74,234, Jun. 9, 1993, Pat. No. 5,413,994.

[30] Foreign Application Priority Data

Jun. 22, 1992 [CH] Switzerland .............................. 1984/92

[51] Int. Cl.$^6$ .................. C07F 9/58; C07F 9/59; C07F 9/6509; A61K 31/675
[52] U.S. Cl. ..................... 514/79; 514/85; 514/89; 514/91; 540/542; 540/544; 544/57; 544/157; 544/337; 546/22; 548/413
[58] Field of Search .............. 546/22; 544/157, 544/57, 337; 540/542, 544; 548/413; 514/89, 85, 79, 91

[56] References Cited

U.S. PATENT DOCUMENTS

| | | | |
|---|---|---|---|
| 4,010,067 | 3/1977 | Hoeger | 562/13 |
| 4,029,697 | 6/1977 | Krueger et al. | 210/700 |
| 4,056,430 | 11/1977 | Hoeger | 162/76 |
| 4,094,782 | 6/1978 | Krueger et al. | 162/76 |
| 5,002,937 | 3/1991 | Bosies et al. | 514/108 |
| 5,360,563 | 11/1994 | Zinke et al. | 252/46.7 |

FOREIGN PATENT DOCUMENTS

| | | | |
|---|---|---|---|
| 0531253 | 3/1993 | European Pat. Off. | 562/13 |
| 8701289 | 3/1987 | WIPO | 562/13 |
| 9103481 | 3/1991 | WIPO | 544/243 |
| 9402492 | 2/1994 | WIPO | 562/13 |

*Primary Examiner*—Alan L. Rotman
*Attorney, Agent, or Firm*—Karen G. Kaiser

[57] ABSTRACT

Compounds of formula I

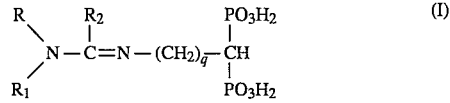

wherein R, $R_1$, $R_2$ and q are as defined in the description, have valuable pharmacological properties and are especially effective as calcium metabolism regulators. They are prepared in a manner known per se.

10 Claims, No Drawings

HETEROCYCLIC AMIDINES USEFUL FOR TREATING DISEASES ASSOCIATED WITH CALCIUM METABOLISM

This is a DIVISIONAL of Ser. No. 08/074,234, filed Jun. 9TH, 1993, now Pat. No. 5,413,994.

The present invention relates to pharmaceutical compositions containing a compound of formula I

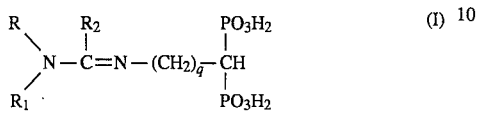

wherein R, $R_1$ and $R_2$ are each independently of one another hydrogen or lower alkyl; or R and $R_1$, taken together, are a bivalent radical $-(CH_2)_m-X-(CH_2)_n-$, (a) wherein m and n are each independently of the other 1 to 6, (b) wherein the sum of m and n is 2 to 7, and (c) wherein X is a $-CH_2-$, $-CH=CH-$, $-O-$, $-N(R_3)-$ or $-S(O)_p-$ group, wherein $R_3$ is hydrogen, lower alkyl, phenyl-lower alkyl or lower alkanoyl, and p is 0 to 2; and q is 0 to 6; or a pharmaceutically acceptable salt thereof, and at least one pharmaceutically acceptable carrier, and also to novel compounds of formula I, to their preparation and to the use of the compounds of formula I for the therapeutic treatment of the human or animal body or for the preparation of pharmaceutical compositions.

The general terms used above and hereinafter have the following preferred meanings within the scope of this application.

The prefix "lower" denotes a radical containing up to 7, preferably up to 4, carbon atoms inclusive.

Lower alkyl is e.g. n-propyl, isopropyl, n-butyl, isobutyl, sec-butyl, tert-butyl, n-pentyl, neopentyl, n-hexyl or n-heptyl, preferably ethyl and, most preferably, methyl.

Phenyl-lower alkyl is e.g. benzyl or 2-phenylethyl.

Halogen is preferably chloro and bromo, but may also be fluoro or iodo.

Lower alkanoyl is e.g. formyl, acetyl, propionyl or pivaloyl.

Typical examples of the group $-NRR_1$, wherein R and $R_1$ together form a bivalent radical $-(CH_2)_m-X-(CH_2)_n-$, where $X=-CH_2-$, are piperidino or pyrrolidino.

Typical examples of the group $-NRR_1$, wherein R and $R_1$ together form a bivalent radical $-(CH_2)_m-X-(CH_2)_n-$, where $X=-CH=CH-$, are dihydro-1H-pyrrol-1-yl or 1,2, 5,6-tetrahydropyridin-1-yl.

Typical examples of the group $-NRR_1$, wherein R and $R_1$ together form a bivalent radical $-(CH_2)_m-X-(CH_2)_n-$, where $X=-O-$, are morpholino or hexahydro-3-oxa- 1H-azepin-1-yl.

Typical examples of the group $-NRR_1$, wherein R and $R_1$ together form a bivalent radical $-(CH_2)_m-X-(CH_2)_n-$, where $X=-N(R_3)-$, are piperazino, 4-methylpiperazino, 4-benzylpiperazino or 4-acetylpiperazino.

Typical examples of the group $-NRR_1$, wherein R and $R_1$ together form a bivalent radical $-(CH_2)_m-X-(CH_2)_n-$, where $X=-S(O)_p-$, are thiomorpholino, S-oxo-thiomorpholino or S,S -dioxothiomorpholino.

Salts of compounds of formula I are, for example, their salts with pharmaceutically acceptable bases, e.g. non-toxic metal salts derived from metals of groups Ia, Ib, IIa and IIb, typically alkali metal salts, preferably sodium or potassium salts, alkaline earth metal salts, preferably calcium or magnesium salts, copper, aluminium or zinc salts, and also ammonium salts with ammonia or organic amines or quaternary ammonium bases, such as free or C-hydroxylated aliphatic amines, preferably mono-, di- or tri-lower alkylamines, typically methylamine, ethylamine or diethylamine, mono-, di- or tris(hydroxy-lower alkyl)amines such as ethanolamine, diethanolamine or triethanolamine, tris(hydroxymethyl)methylamine or 2-hydroxy-tert-butylamine, or N-(hydroxy-lower alkyl)-N,N-di-lower alkylamines and N-(polyhydroxy-lower alkyl)-N-lower alkylamines such as 2-(dimethylamino)ethanol or D-glucamine, or quaternary aliphatic ammonium hydroxides such as tetrabutylammonium hydroxide. Comprised are complete as well as partial salts, i.e., for example, salts with 1, 2, 3 or 4 equivalents, preferably with 2 equivalents, of base per mol of acid of formula I.

Pharmaceutically unsuitable salts such as picrates or perchlorates may also be used for isolating and purifying the compounds of formula I. Only the pharmaceutically acceptable non-toxic salts are used for therapeutic use, for which reason they are preferred.

The compounds of formula I and their salts have valuable pharmacological properties. They exert in particular a regulatory action on the calcium metabolism of warm-blooded animals. For example, they induce a marked inhibition of bone resorption in rats, as can be demonstrated in the assay described in Acta Endocrinol. 78, 613–24 (1975), and also in the PTH-induced rise in the serum calcium level after subcutaneous administration in doses of c. 0.01 to c. 1.0 mg/kg, as well as in the TPTX (thyroparathyroidectomised) rat model from the experimental hypercalcemia induced by vitamin $D_3$ after administration of doses of c. 0.0005 to c. 0.5 mg/kg s.c. In like manner, the tumour hypercalcemia induced by Walker 256 tumours is inhibited after administration of c. 1.0 to c.100 mg/kg. In adjuvants arthritis in rats they also markedly inhibit the progression of chronic arthritic processes in the assay of Newbold, Brit. J. Pharmacology 21, 127 (1963) and of Kaibara et at., J. Exp. Med. 159, 1388–96 (1984), when administered in doses of c. 0.01 to c. 1.0 mg/kg s.c.

The compounds of formula I and their salts are therefore admirably suitable for use as medicaments for, inter alia, the treatment of diseases which are associated with disorders of calcium metabolism, in particular tumour-induced hypercalcemia, bone metastases and Paget's disease, as well as for the treatment of inflammatory processes in joints, degenerative processes in particular cartilage, osteoporosis, periodontitis, hyperparathyroidism, and also, inter alia, for the treatment of calcium deposits in blood vessels or in prothetic implants.

From among the pharmaceutical compositions referred to above containing a compound of formula I, those compositions merit particular interest which contain a compound of formula I, wherein R and $R_1$ are each independently of the other lower alkyl, or R and $R_1$ together are a bivalent radical $-(CH_2)_m-X-(CH_2)_n-$ as defined above, and $R_2$ is hydrogen or lower alkyl, or a pharmaceutically acceptable salt thereof.

The invention relates preferably to pharmaceutical compositions containing a compound of formula I, wherein R and $R_1$ are each independently of the other lower alkyl, or R and $R_1$ together with the linking nitrogen atom form a group selected from among piperidino, pyrrolidino, dihydro-1H-pyrrol-1-yl, 1,2,5,6-tetrahydropyridin-1-yl, morpholino, hexahydro-3-oxa- 1H-azepin-1-yl, piperazino, 4-lower alkyl-piperazino, 4-phenyl-lower alkylpiperazino, 4-lower alkanoylpiperazino, thiomorpholino, S-oxothiomorpholino or S,S-dioxothiomorpholino, $R_2$ is hydrogen or lower alkyl, and q is 0 to 6; or a pharmaceutically acceptable salt thereof and at least one pharmaceutically acceptable carrier.

Particularly preferred pharmaceutical compositions contain a compound of formula I, wherein R and $R_1$ are each independently of the other lower alkyl, or R and $R_1$ together with the linking nitrogen atom form a group selected from among piperidino, pyrrolidino, morpholino, piperazino or thiomorpholino, $R_2$ is hydrogen or lower alkyl, and q is 0; or a pharmaceutically acceptable salt thereof and at least one pharmaceutically acceptable carrier.

The invention relates more particularly to pharmaceutical compositions containing a compound of formula I, wherein R and $R_1$ are each independently of the other methyl or ethyl, $R_2$ is hydrogen, and q is 0, for example N,N-dimethyl-formamidinomethanebisphosphonic acid, or a pharmaceutically acceptable salt thereof and at least one pharmaceutically acceptable carrier.

The invention further relates to novel compounds of formula I

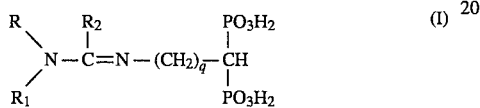

wherein R, $R_1$ and $R_2$ are each independently of one another hydrogen or lower alkyl; or R and $R_1$, taken together, are a bivalent radical —$(CH_2)_m$—X—$(CH_2)_n$—, (a) wherein m and n are each independently of the other 1 to 6, (b) wherein the sum of m and n is 2 to 7, and (c) wherein X is a —$CH_2$—, —CH=CH—, —O—, —$N(R_3)$— or —$S(O)_p$— group, wherein $R_3$ is hydrogen, lower alkyl, phenyl-lower alkyl or lower alkanoyl, and p is 0 to 2; and q is 0 to 6; with the proviso that $R_2$ is different from hydrogen when q is 0 and both substituents $R_1$ and $R_2$ are each independently of the other hydrogen, methyl or ethyl; or salts thereof.

Compounds meriting particular interest from among the compounds of formula I mentioned above are those wherein R and $R_1$ are each independently of the other lower alkyl, or R and $R_1$, taken together, are a bivalent radical —$(CH_2)_m$—X—$(CH_2)_n$—, as defined above, and $R_2$ is hydrogen or lower alkyl, and salts thereof.

The invention relates preferably to the compounds of formula I, wherein R and $R_1$ are each independently of the other lower alkyl, or R and $R_1$ together with the linking nitrogen atom are a group selected from among piperidino, pyrrolidino, dihydro-1H-pyrrol-1-yl, 1,2,5,6-tetrahydropyridin-1-yl, morpholino, hexahydro-3-oxa- 1H-azepin-1-yl, piperazino, 4-lower alkylpiperazino, 4-phenyl-lower alkyl-piperazino, 4-lower alkanoylpiperazino, thiomorpholino, S-oxothiomorpholino or S,S-dioxothiomorpholino, $R_2$ is hydrogen or lower alkyl, and q is 0 to 6; with the proviso that $R_2$ is different from hydrogen when q is 0 and both substituents $R_1$ and $R_2$ are each independently of the other methyl or ethyl; or a pharmaceutically acceptable salt thereof.

Particularly preferred compounds of formula I are those wherein R is $C_1$–$C_7$alkyl and $R_1$ is $C_3$–$C_7$alkyl; or R and $R_1$ together with the linking nitrogen atom form a group selected from among piperidino, pyrrolidino, morpholino, piperazino or thiomorpholino, $R_2$ is hydrogen or lower alkyl, and q is 0; or a pharmaceutically acceptable salt thereof.

The invention relates first and foremost to the specific compounds described in the Examples, and salts thereof.

The novel compounds of formula I can be prepared in per se known manner, for example by a) in a compound of formula II

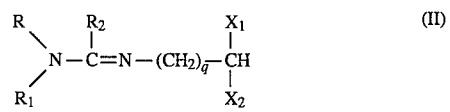

wherein R, $R_1$, $R_2$ and q are as defined for formula I, $X_1$ is a functionally modified phosphono group and $X_2$ is a free or functionally modified phosphono group, converting functionally modified phosphono $X_1$ and optionally $X_2$ into the free phosphono group, or b) reacting a compound of formula III,

wherein R, $R_1$ and $R_2$ are as defined for formula I, or a functional derivative thereof, with a compound of formula IV,

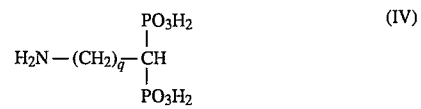

wherein q is as defined for formula I, or a suitable salt thereof; and, if desired, converting a compound of formula I so obtained into another compound of formula I, and/or, if desired, converting a salt into the free compound or into another salt, and/or, if desired, converting a free compound of formula I with salt-forming properties into a salt.

The reactions used in the practice of this invention and the preparation of novel starting materials and/or intermediates are carried out in general accordance with the mode of obtaining known starting materials and/or intermediates using, even if not expressly mentioned hereinafter, the customary auxiliaries such as catalysts, condensing and solvolysis agents and/or solvents and diluents, and reaction conditions such as temperature and pressure as well as optional inert gases.

In the more detailed description of processes a)–b), the symbols R, $R_1$, $R_2$ and q are each as defined for formula I, unless otherwise indicated.

In process variant a), functionally modified phosphono groups to be converted into phosphono are typically in ester form, preferably a diester form of formula —P(=O)(OR)$_2$ (IIa), wherein OR is etherified hydroxy, preferably lower alkoxy, lower alkanoyloxy-lower alkoxy, or a phenoxy or α-phenylphenoxy group which is unsubstituted or substituted by lower alkyl, lower alkoxy, halogen, trifluoromethyl and/or hydroxy, or is silyloxy such as tri-lower alkylsilyloxy.

The conversion of functionally modified phosphono groups into free phosphono groups is effected in conventional manner, for example by hydrolysis, conveniently in the presence of a mineral acid such as hydrochloric acid or sulfuric acid in the temperature range from c. 80° C. to c. 110° C., for example at boiling heat, or by reaction with a tri-lower alkylhalosilane, e.g. trimethylsilane or, preferably, trimethyliodosilane or trimethylbromosilane, preferably in methylene chloride in the temperature range from c. 0° C. to c. 40° C., and subsequent treatment with water. α-Phenyl-lower alkyl esters can further be converted into compounds of formula I by hydrogenolysis, typically by reaction with hydrogen in the presence of a hydrogenation catalyst such as a nickel or noble metal catalyst, e.g. palladium on carbon, preferably in a lower alkanol under normal conditions of temperature and pressure.

The starting materials of formula II may for example be prepared by reacting a compound of formula III with a compound of formula V

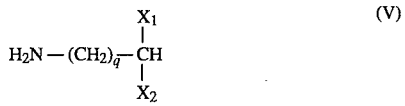

wherein $X_1$ is a functionally modified phosphono group and $X_2$ is a free or functionally modified phosphono group.

Process (b): It is preferred to use a functional derivative of a compound of formula III.

A functional derivative of a compound of formula HI is typically an acetal, preferably a di-lower alkyl acetal or lower alkylene acetal, most preferably a dimethyl acetal.

The reaction of process (b) can be carried out in the presence of a condensing agent, e.g. $POCl_3$, or also without a condensing agent.

Compounds of formula I obtainable by the inventive process can also be converted in conventional manner into other compounds of formula I.

The above described reactions can be carried out under per se known reaction conditions with or without solvents or diluents, preferably those that are inert to the reactants and dissolve them, in the absence or presence of catalysts, condensing agents or neutralising agents, depending on the type of reaction and/or reactants, at reduced, normal or elevated temperature, e.g. in the temperature range from c. −70 to c. +190° C., preferably from c. −20 to c. +150° C., for example at the boiling point of the solvent employed, under atmospheric pressure or in a closed reactor, under normal or elevated pressure, and/or in an inert atmosphere, for example in a nitrogen atmosphere.

Depending on the choice of starting materials and procedures, the novel compounds can be obtained in the form of one of the possible isomers, e.g. optical isomers in accordance with the number of asymmetric carbon atoms, conveniently in the form of enantiomers such as antipodes, diastereoisomers, or mixtures thereof, for example mixtures of enantiomers such as racemates, mixtures of diastereoisomers or mixtures of racemates.

Mixtures of diastereoisomers and mixtures of racemates can be separated into the pure isomers or racemates in known manner on the basis of the physico-chemical differences between the components, conveniently by chromatography and/or fractional distillation.

Further, salt-forming compounds can be converted in a manner known per se into salts, conveniently by reacting a solution of the free compound in a suitable solvent or mixture of solvents with an appropriate base or with a suitable ion exchanger.

Salts can be converted in a manner known per se into the free compounds, typically by treatment with an acid such as a mineral acid, e.g. hydrochloric acid.

Salts can be convened in a manner known per se into other salts, typically by treatment with a suitable base such as sodium hydroxide or potassium hydroxide, ammonia or a suitable amine.

Because of the close relationship between the novel compounds in the free form and in the form of their salts, the references made throughout this specification to the free compounds and their salts also applies by analogy to the corresponding salts and free compounds.

The compounds of formula I, including their salts, can also be obtained in the form of hydrates or may include the solvent used for crystallisation.

The invention also relates to those embodiments of the process in which a compound obtainable as intermediate is used as starting material and the missing steps are carried out or a starting material is used in the form of a salt or, preferably, is formed under the reaction conditions.

The novel starting materials which have been developed specially for the synthesis of the novel compounds, especially the choice of starting materials leading to the compounds of formula I referred to at the outset as preferred, the processes for their preparation and the use thereof as intermediates, likewise constitute an object of the invention.

The novel pharmaceutical compositions contain a therapeutically effective mount of active ingredient, without or together with inorganic or organic solid or liquid pharmaceutically acceptable careers that are suitable for enteral, for example oral, parenteral or transdermal administration. Thus tablets or gelatin capsules are used that contain the active ingredient together with a diluent such as lactose, dextrose, saccharose, mannitol, sorbitol, cellulose and/or glidants, typically diatomaceous earth, talcum, stearic acid or salts thereof such as magnesium or calcium stearate, and/or polyethylene glycol. Tablets may also contain binders such as magnesium aluminium silicate, starches such as corn, rice, or arrowroot starch, gelatin, tragacanth, methyl cellulose, sodium carboxymethyl cellulose and/or polyvinyl pyrrolidone and, if desired, disintegrators such as starches, agar, alginic acid or a salt thereof, e.g. sodium alginate, and/or effervescent mixtures, or absorbents, colorants, flavourings and sweeteners. The novel compounds of formula I can also be used in the form of compositions for parenteral administration or of infusion solutions. Such solutions are preferably isotonic aqueous solutions or suspensions which, in the case of lyophilised compositions that contain the active ingredient by itself or together with a carrier such as mannitol, can be prepared before use. The pharmaceutical compositions can be sterilised and/or can contain adjuvants such as preservatives, stabilisers, wetting agents and/or emulsifiers, solubilisers, salts for regulating the osmotic pressure and/or buffers. The novel pharmaceutical compositions which, if desired, may contain further pharmacologically active substances, are prepared in per se known manner by conventional mixing, granulating, sugar-coating, solution or lyophilising methods and contain from about 0.1% to 100%, preferably from about 1% to about 50%, and in the case of lyophilisates up to about 100%, of active ingredient.

Suitable compositions for parenteral administration are in particular aqueous solutions of the active ingredient in water-soluble form, typically in the form of a water-soluble pharmaceutically acceptable salt, and also suspensions of the active ingredient such as oily injection suspensions using suitable lipophilic solvents or vehicles such as fatty oils, typically sesame oil, or synthetic fatty acid esters such as ethyl oleate, and also triglycerides, or aqueous injection suspensions that contain viscosity increasing substances, e.g. sodium carboxymethyl cellulose, sorbitol and/or dextran, and to which stabilisers may be added.

Suitable formulations for transdermal administration contain an effective amount of a novel compound with a carrier. Useful careers comprise absorbable pharmacological suitable solvents to assist passage of the active ingredient through the skin. Transdermal delivery systems are normally in the form of a patch comprising (a) a substrate, (b) a reservoir containing the active ingredient and optional carriers, (c) a membrane that releases the active ingredient to the skin at a controlled and determined rate over a prolonged period of time, and (d) means for attaching the system to the skin.

The invention further relates to the use of compounds of formula I for the treatment of diseases associated with disorders of calcium metabolism, preferably by providing pharmaceutical compositions. The dosage of the compound of formula I can depend on a variety of factors such as mode of administration, species, age and/the individual condition of the patient. Single doses will typically contain from about 0.01 to about 0.1 mg, preferably from 0.02 to 0.08 mg for parenteral administration, and from about 0.2 to about 2.5 mg, preferably from 0.3 to 1.5 mg, for oral administration, in each case per kilogram of bodyweight. The preferred single doses are thus from about 0.5 to 5.0 mg for parenteral administration and from about 10 to 100 mg for oral administration. The daily doses for oral administration are from about 0.25 to about 10 mg/kg and, for warm-blooded animals having a bodyweight of about 70 kg, preferably from about 20 mg to about 500 mg.

The invention is illustrated by the following Examples. Pressures are given in mbar.

EXAMPLE 1

3.9 g (0.0097 mol) of crude tetraethyl N-butyl-N-methylformamidinomethanebisphosphonate are dissolved in 30 ml of methylene chloride and to the solution are added 6.3 ml (0.049 mol) of trimethylbromosilane at 0° C. The reaction mixture is allowed to stand for 72 hours at room temperature and the solvent is then removed under reduced pressure. The residual oil is dissolved in 95% aqueous methanol by heating. N-Butyl-N-methylformamidinomethanebisphosphonic acid precipitates from the cooled solution in colourless crystals with a melting point of 200°–201° C. (dec.).

The starting compound is prepared as follows:

3.03 g (0.01 mol) of tetraethyl aminomethylenebisphosphonate are stirred with 1.61 g (0.01 mol) of N-butyl-N-methylformamide dimethyl acetal in 30 ml of tetrahydrofuran for 5 hours under reflux. The solvent is then removed by distillation, giving crude tetraethyl N-butyl-N-methylformamidinomethane bisphosphonate, which is further used without purification.

EXAMPLE 2

The general procedure described in Example 1 is repeated, but replacing N-butyl-N-methylformamide dimethyl acetal with N-butyl-N-methylacetamide dimethyl acetal in the preparation of the starting compound, to give N-butyl-N-methylacetamidinomethanebisphosphonic acid which melts at 209°–211 ° C. (dec.).

The starting compound is prepared as follows:

6.1 g (0.07 mol) of n-butylmethylamine are stirred with 9.3 g (0.07 mol) of N,N-dimethylacetamide dimethyl acetal for 24 hours under reflux at a bath temperature of 130° C. Subsequent vacuum distillation gives N-butyl-N-methylacetamide dimethyl acetal, bp 72°–75° C./31 mbar.

EXAMPLE 3

2.8 g (0.007 mol) of tetraethyl piperidino-formamidinomethane bisphosphonate are dissolved in 25 ml of dichloromethane and to the solution are added 4.5 ml (0.035 mol) of trimethylbromosilane. The reaction mixture is allowed to stand for 72 hours at room temperature and then the solvent is removed under reduced pressure. The residual oil is taken up in in hot aqueous 95% methanol, whereupon piperidinoformamidinomethanebisphosphonic acid crystallises; mp. 235°–236° C.

The starting material is prepared as follows:

1.27 g (0.008 mol) of piperidinoformamide dimethyl acetal [Liebigs Ann. 641 (1961) 1] and 2.43 g (0.008 mol) of tetraethyl aminomethylenebisphosphonate are dissolved in 30 ml of tetrahydrofuran (THF) and the solution is refluxed for 6 hours. The solvent is then removed under reduced pressure, giving crude tetraethyl piperidinoformamidinomethanebisphosphonate, which is further used without purification.

EXAMPLE 4

The following compounds can be prepared in accordance with the general procedures described in Examples 1–3:

(a) pyrrolidinoformamidinomethanebisphosphonic acid, and (b) 2-(N,N-dimethylformamidino)ethane- 1,1-bisphosphonic acid

EXAMPLE 5

3.0 g (0.008 mol) of tetraethyl pyrrolidinoformamidinomethanebisphosphonate are dissolved in 25 ml of dichloromethane and to the solution are added 4.5 ml (0.035 mol) of trimethylbromosilane. The reaction mixture is allowed to stand for 72 hours at room temperature and then the solvent is removed under reduced pressure. The residual oil is taken up in in hot aqueous 95% methanol, whereupon the monohydrate of pyrrolidinoformamidinomethanebisphosphonic acid crystallises with a melting point of 213°–214° C. (dec.).

The starting material is prepared as follows:

2.43 g (0.008 mol) of tetraethyl aminomethylenebisphosphonate and 1.20 g (0.0082 mol) of 1-(dimethoxymethyl)pyrrolidine are dissolved in 30 ml of THF and the solution is heated to the boil for 40 hours under reflux. The solvent is stripped off under reduced pressure, giving crude tetraethyl pyrrolidinoformamidinomethanebisphosphonate, which is further used without purification.

EXAMPLES 6

Tablets each containing 50 mg of active ingredient, e.g. N,N-dimethylformamidinomethanebisphosphonic acid or a salt thereof, e.g. the disodium salt, can be prepared as follows:

| Composition (10 000 tablets) | |
|---|---|
| active ingredient | 500.0 g |
| lactose | 500.0 g |
| potato starch | 325.0 g |
| gelatin | 8.0 g |
| talcum | 60.0 g |
| magnesium stearate | 10.0 g |
| silica (highly dispersed) | 20.0 g |
| ethanol | q.s. |

The active ingredient is mixed with the lactose and 292 g of potato starch. The mixture is moistened with an ethanolic solution of gelatin and granulated through a sieve. The granulate is dried and the remainder of the potato starch, the talcum, the magnesium stearate and the silica are added and the mixture is compressed to 145.0 g tablets containing 50.0 g of active ingredient. If desired, the tablets can be provided with a breaking notch for finer adjustment of the dose.

EXAMPLE 7

Film-coated tablets each containing 100 mg of active ingredient, e.g. N-butyl-N-methylformamidinomethanebisphosphonic acid or a salt thereof, e.g. the disodium salt, can be prepared as follows:

| Composition (for 1000 film-coated tablets) | |
| --- | --- |
| active ingredient | 100.0 g |
| lactose | 100.0 g |
| corn starch | 70.0 g |
| talcum | 8.5 g |
| calcium stearate | 1.5 g |
| hydroxypropyl methyl cellulose | 2.35 g |
| shellac | 0.64 g |
| water | q.s. |
| methylene chloride | q.s. |

The active ingredient, the lactose and 40 g of corn starch are mixed and moistened with a paste prepared from 15 g of corn starch and water (with heating), and the mixture is granulated. The granulate is dried, the remainder of the corn starch, the talcum and the calcium stearate are added and mixed with the granulate. The mixture is compressed to 280 mg tablets which are coated with a solution of hydroxypropyl methyl cellulose and shellac in methylene chloride. Final weight of the tablets: 283 mg.

EXAMPLE 8

Hard gelatin capsules containing 100 g of active ingredient, e.g. N-butyl-N-methylacetamidinomethanebisphosphonic acid or a salt thereof, e.g. the disodium salt, can be prepared as follows:

| Composition (for 1000 capsules) | |
| --- | --- |
| active ingredient | 100.0 g |
| microcrystalline cellulose | 30.0 g |
| sodium lauryl sulfate | 2.0 g |
| magnesium stearate | 8.0 g |

The sodium lauryl sulfate is sieved through a sieve having a mesh size of 0.2 mm and added to the lyophilised active ingredient and both components are thoroughly mixed. The microcrystalline cellulose is passed through a sieve having a mesh size of 0.9 ram, added to the above mixture, and the ingredients are throughly mixed once more for 10 minutes. Finally, the magneisum stearate is passed through a sieve having a mesh size of 0.8 min. After mixing for 3 minutes, size 0 hard gelatin capsules are each filled with 390 mg of the formulation so obtained.

EXAMPLE 9

A 0.2% injection or infusion solution of piperidinoformamidinomethanebisphosphonic acid or a salt thereof, e.g. the disodium salt, can be prepared as follows:

| Composition (for 1000 ampoules) | |
| --- | --- |
| active ingredient | 5.0 g |
| sodium chloride | 22.5 g |
| phosphate buffer pH = 7.4 | 300.0 g |
| demineralised water | ad 2500.0 ml |

The active ingredient is dissolved in 1000 ml of water and filtered through a microfilter. The buffer solution is added, followed by the addition of water to make up 2500 ml. To prepare dosage unit forms, 1.0 or 2.5 ml of the solution are filled into glass ampoules each containing 2.0 or 5.0 mg of active ingredient.

EXAMPLE 10

In general accordance with the procedures described in the foregoing Examples 6 to 9 it is possible to prepare pharmaceutical compositions containing another compound of formula I according to any one of Examples 1 to 5.

What is claimed is:

1. A pharmaceutical composition containing a therapeutically effective amount for the treatment of diseases associated with disorders of calcium metabolism of a compound of formula I

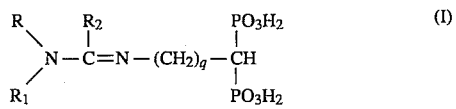

wherein $R_2$ is hydrogen or lower alkyl; R and $R_1$, taken together, are a bivalent radical $-(CH_2)_m-X-(CH_2)_n-$, (a) wherein m and n are each independently of the other 1 to 6, (b) wherein the sum of m and n is 2 to 7, and (c) wherein X is a $-CH_2-$, $-CH=CH-$, $-O-$, $-N(R_3)-$ or $-S(O)_p-$ group, wherein $R_3$ is hydrogen, lower alkyl, phenyl-lower alkyl or lower alkanoyl, and p is 0 to 2; and q is 0 to 6; or a pharmaceutically acceptable salt thereof, and at least one pharmaceutically acceptable carrier.

2. A pharmaceutical composition according to claim 1, R and $R_1$ together with the linking nitrogen atom form a group selected from among piperidino, pyrrolidino, dihydro-1H-pyrrol-1-yl, 1,2,5,6-tetrahydropyridin-1-yl, morpholino, hexahydro-3-oxa-1H-azepin-1-yl, piperazino, 4-lower alkyl-piperazino, 4-phenyl-lower alkylpiperazino, 4-lower alkanoylpiperazino, thiomorpholino, S-oxothiomorpholino and S,S-dioxothiomorpholino, $R_2$ is hydrogen or lower alkyl, and q is 0 to 6; or a pharmaceutically acceptable salt thereof, and at least one pharmaceutically acceptable carrier.

3. A pharmaceutical composition according to claim 1, R and $R_1$ together with the linking nitrogen atom form a group selected from among piperidino, pyrrolidino, morpholino, piperazino, and thiomorpholino, $R_2$ is hydrogen or lower alkyl, and q is 0; or a pharmaceutically acceptable salt thereof, and at least one pharmaceutically acceptable carrier.

4. A pharmaceutical composition according to claim 1, which contains piperidinoformamidinomethanebisphosphonic acid, or a pharmaceutically acceptable salt thereof, and at least one pharmaceutically acceptable carrier.

5. A compound of formula I

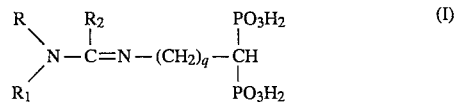

wherein $R_2$ is hydrogen or lower alkyl; R and $R_1$, taken together, are a bivalent radical —$(CH_2)_m$—X—$(CH_2)_n$—, (a) wherein m and n are each independently of the other 1 to 6, (b) wherein the sum of m and n is 2 to 7, and (c) wherein X is a —$CH_2$—, —CH=CH—, —O—, —$N(R_3)$— or —$S(O)_p$— group, wherein $R_3$ is hydrogen, lower alkyl, phenyl-lower alkyl or lower alkanoyl, and p is 0 to 2; and q is 0 to 6; or a salt thereof.

6. A compound of formula I according to claim 5, wherein R and $R_1$ together with the linking nitrogen atom are a group selected from among piperidino, pyrrolidino, dihydro-1H-pyrrol-1-yl, 1,2,5,6-tetrahydropyridin-1-yl, morpholino, hexahydro-3-oxa-1H-azepin-1-yl, piperazino, 4-lower alkylpiperazino, 4-phenyl-lower alkyl-piperazino, 4-lower alkanoylpiperazino, thiomorpholino, S-oxothiomorpholino and S,S-dioxothiomorpholino, $R_2$ is hydrogen or lower alkyl, and q is 0 to 6; or a pharmaceutically acceptable salt thereof.

7. A compound of formula I according to claim 5, wherein R and $R_1$ together with the linking nitrogen atom form a group selected from among piperidino, pyrrolidino, morpholino, piperazino and thiomorpholino, $R_2$ is hydrogen or lower alkyl, and q is 0; or a pharmaceutically acceptable salt thereof.

8. Piperidinoformamidinomethanebisphosphonic acid according to claim 5, or a pharmaceutically acceptable salt thereof.

9. A pharmaceutical composition which contains a therapeutically effective amount for the treatment of diseases associated with disorders of calcium metabolism of a compound according to claim 5 or a pharmaceutically acceptable salt thereof and at least one pharmaceutically acceptable carder.

10. A method of treating a disease associated with disorders of calcium metabolism in a mammal in need thereof comprising administering to said mammal an effective amount for treating said disease of a compound according to claim 5 or a pharmaceutically acceptable salt thereof.

* * * * *